US00PP08004P

United States Patent [19]

Devries

[11] Patent Number: Plant 8,004

[45] Date of Patent: Oct. 13, 1992

[54] VARIETY OF BEGONIA NAMED SUSANNE

[75] Inventor: Richard Devries, Niagara on the Lake, Canada

[73] Assignee: Schenck Farms & Greenhouses Co. Limited, Ontario, Canada

[21] Appl. No.: 628,499

[22] Filed: Dec. 17, 1990

[51] Int. Cl.[5] ..... A01H 5/00
[52] U.S. Cl. ..... Plt./87.18
[58] Field of Search ..... Plt./68

[56] References Cited

U.S. PATENT DOCUMENTS

P.P. 5,179 1/1984 Schelbeck ..... Plt. 68
P.P. 5,390 1/1985 Boll ..... Plt. 68
P.P. 6,186 5/1988 Hvid ..... Plt. 68

*Primary Examiner*—James R. Feyrer
*Attorney, Agent, or Firm*—Webb, Burden, Ziesenheim & Webb

[57] ABSTRACT

The new variety is characterized by a self-supporting, vigorous plant having prolific and long-lasting blooms and good basal branching. The dark foliage contrasts nicely against the red bloom.

1 Drawing Sheet

BACKGROUND OF THE INVENTION

The present invention comprises a new and distinct cultivar of *Begonia*×*hiemalis* known by the varietal name Susanne. The new variety originated as a sport of Pia Elise (U.S. Plant Pat. No. 5,930) and was discovered on Jul. 14, 1987 at Schenck Farms and Greenhouses Co. Limited in St. Catharines, Ontario, Canada. The new variety was first asexually reproduced by cuttings at Schenck Farms and Greenhouses Co. Limited in St. Catharines, Ontario, Canada. The new variety has been asexually reproduced by cuttings at Oglevee, Ltd. in Connellsville, Pa. over a three-year period and has been found to retain its distinctive characteristics. Susanne has the same plant form as Pia Elise, but has darker foliage and a red flower instead of a pink flower.

The cultivar when grown in a glass greenhouse in Connellsvile, Pa. using natural light and 65° F. night and 72° F. day, has a response time of 9 to 10 weeks from a rooted cutting to flowering in a 6 inch pot (no pinch). The test plants were potted in May of 1990 in a peat-lite mix and fertilized with Peters 20-10-20 fertilizer.

The following characteristics distinguish 'Susanne' from the parent cultivar 'Pia Elise' (U.S. Plant Pat. No. 5,390) and other begonias patented and/or commercially known and used in the floricultural industry, namely 'Barbara' (U.S. Plant Pat. No. 5,179) and 'Lisa' (U.S. Plant Pat. No. 6,186):

1. This mutation has the same overall plant form as 'Pia Elise' and 'Barbara'.

2. It is more vigorous and has a slightly larger overall leaf size then 'Lisa'.

3. The flowers of 'Suzanne' are double and have the same size as 'Pia Elise', they are slightly less double and larger in diameter than 'Barbara'.

4. The foliage color of mature expanded leaves is Greyed/Purple 183B as compared to Yellow/Green 147 on 'Pia Elise' and Yellow/Green 147 on 'Lisa'. The substantial difference in color of the foliage clearly distinguishes this mutation from both 'Pia Elise' and 'Lisa'.

5. This mutation has a medium to dark red flower (Red Group 43A) as opposed to the light red flower of 'Lisa' (HCC 19/1 - HCC 622/1, which is believed to be roughly comparable to 43C which is at least two shades lighter than 43A).

DESCRIPTION OF THE DRAWING

FIG. 1 of the accompanying photographic drawing illustrates the new cultivar the color being as nearly true as possible with color illustrations of this type.

DESCRIPTION OF THE NEW PLANT

The following detailed description sets forth the characteristics of the new cultivar. The data which defines these characteristics were collected by asexual reproduction carried out by Oglevee, Ltd. in Connellsville, Pa. The plant history was taken on 9 to 10 week plants blossomed under natural light in a greenhouse and the color readings were taken indoors under 200 foot candles of florescent cool white light. Color reference are primarily to the R.H.S. Colour Chart of The Royal Horticultural Society of London.

THE PLANT

Classification:
- *Botanical.*—*Begonia*×*hiemalis.*
- *Commercial.*—Begonia.

Flower:
- *Fully Expanded.*—5-6 cm. in diameter.
- *Borne.*—Compound dichesium (cyme).
- *Stems.*—Strong and upright. Color group Red Group 44C.
- *Form.*—Fully double. Each flower has 2 sepals, 7-8 petals and 7-10 petaloids.
- *Permanence.*—Long lasting bloom, lasts an average of 2-3 weeks.

Color:
- *Tonality from a Distance.*—Flowers appear Red.
- *Front of Petals.*—Characterized by Red Group 43A.
- *Reverse of Petals.*—Red Group 48C.
- *Base of Petals.*—Red Group 48C.

Petals:
- *Texture.*—Crepe paper like (gentle crinkles).
- *Appearance.*—Oval.
- *Arrangement*—Semi to fully double.

*Persistence*—Very good flower response, produces many bud.

*Fragrance.*—None.

Reproductive organs: None.

Plant:

*Form.*—Good basal branching, internodes 2-3 cm. apart, strong stems give good self-support.

*Growth.*—Very vigorous.

*Height from soil line.*—25-27 cm.

*Spread.*—22-24 cm.

Foliage:

*Size.*—12 cm. length; 9 cm. width.

*Quantity.*—Very abundant.

*Shape.*—Acute tip with irregularly lobed attachment; edge is double serrated.

*Top side.*—Color gradient young leaves, Greyed/-Purple Group 183B; mature expanded leaves, Green Group 137A.

*Underside.*—Color: Yellow/Green Group 147D.

*Ribs and veins.*—Smooth on top; raised on bottom. Veins on lower side define the only area where tricomes (hairs) appear. Color: Top Side — Yellow/Green Group 144C; Bottom Side — Red Group 37A.

GENERAL CHARACTERISTICS

The Susanne Begonia exhibits vigorous plant growth, good basal branching and produces many buds. The dark foliage contrasts nicely against the red bloom.

I claim:

1. A new and distinct variety of Begonia plant substantially as shown and described.

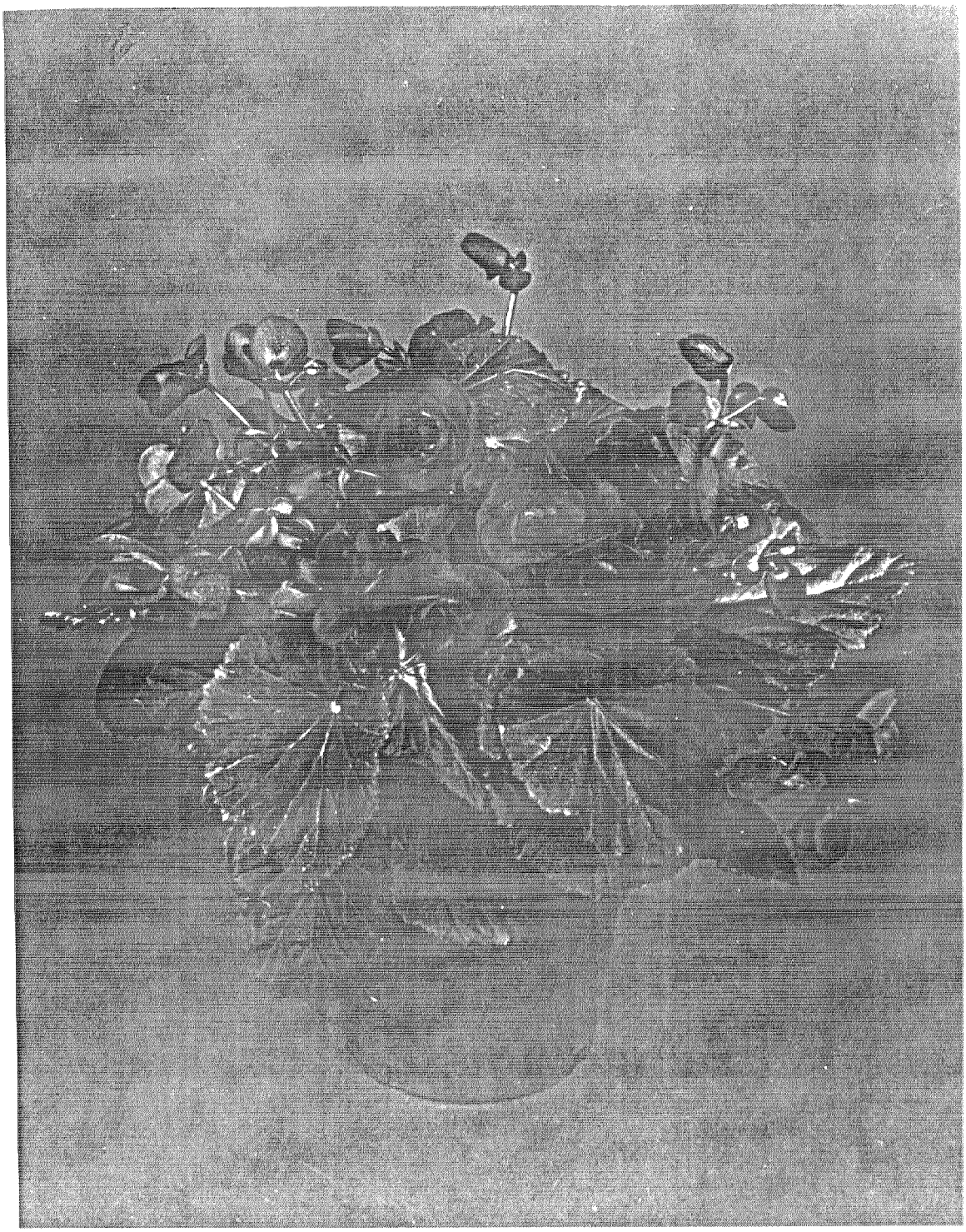

* * * * *